(12) United States Patent
Kim et al.

(10) Patent No.: US 10,475,545 B2
(45) Date of Patent: Nov. 12, 2019

(54) THREE-STAGE CARRIER FOR GAMMA IRRADIATION AND GAMMA IRRADIATION METHOD USING THREE-STAGE CARRIER

(71) Applicant: GREENPIA TECHNOLOGY INC, Gyeonggi-do (KR)

(72) Inventors: Kwansoo Kim, Seoul (KR); Kwanghoon Kim, Gyeonggi-do (KR); Soojin Kim, Gyeonggi-do (KR); Hoochul Lee, Gyeonggi-do (KR); Yongwoon Eom, Gyeonggi-do (KR)

(73) Assignee: GREENPIA TECHNOLOGY INC, Gyeonggi-Do (KR)

( * ) Notice: Subject to any disclaimer, the term of this patent is extended or adjusted under 35 U.S.C. 154(b) by 0 days.

(21) Appl. No.: 15/775,684

(22) PCT Filed: Oct. 21, 2016

(86) PCT No.: PCT/KR2016/011938
§ 371 (c)(1),
(2) Date: May 11, 2018

(87) PCT Pub. No.: WO2017/086616
PCT Pub. Date: May 26, 2017

(65) Prior Publication Data
US 2018/0358143 A1 Dec. 13, 2018

(30) Foreign Application Priority Data

Nov. 16, 2015 (KR) .......................... 10-2015-0160349

(51) Int. Cl.
*G21K 5/10* (2006.01)
*A61L 2/08* (2006.01)
(Continued)

(52) U.S. Cl.
CPC .................. *G21K 5/10* (2013.01); *A61L 2/08* (2013.01); *A61L 2/081* (2013.01); *A61L 2/24* (2013.01); *G21K 5/08* (2013.01)

(58) Field of Classification Search
CPC .... G21K 5/10; G21K 5/08; A61L 2/08; A61L 2/081; A61L 2/24
See application file for complete search history.

(56) References Cited

U.S. PATENT DOCUMENTS

| 4,281,954 A | * | 8/1981 | Bosshard | B65G 1/0414 414/287 |
| 5,396,074 A | * | 3/1995 | Peck | G21K 5/10 250/453.11 |
| 5,712,894 A | * | 1/1998 | Lanotte | A61L 2/202 378/68 |

FOREIGN PATENT DOCUMENTS

| JP | 60-76700 A | 5/1985 |
| JP | 60076700 A | * 5/1985 |

(Continued)

OTHER PUBLICATIONS

International Search Report for PCT/KR2016/011938.

*Primary Examiner* — David E Smith
(74) *Attorney, Agent, or Firm* — The PL Law Group, PLLC

(57) ABSTRACT

A three-stage carrier is transported to an irradiation room by transporting means and is irradiated with gamma ray sources installed on ray source rack such that a product loaded therein is treated. The three-stage carrier includes a central container in a center of the three-stage carrier; an upper container formed on the central container; and a lower container formed under the central container. Here, the central container, the upper container, and the lower container are partitioned by septum, a height of the three-stage carrier is greater than a height of the ray source lack, and the (Continued)

central container has a height greater than a height of the upper container or a height of upper container. The better quality stability through uniform sterilization and the improved energy utilization efficiency and productivity, the reduction of cost may be achieved.

6 Claims, 11 Drawing Sheets

(51) Int. Cl.
*A61L 2/24* (2006.01)
*G21K 5/08* (2006.01)

(56) References Cited

FOREIGN PATENT DOCUMENTS

| | | |
|---|---|---|
| JP | 8-215292 A | 8/1996 |
| KR | 2002-0020756 A | 3/2002 |
| KR | 10-1589917 B1 | 1/2016 |
| WO | WO 98/50939 A1 | 11/1998 |

* cited by examiner

Prior Art

Prior Art

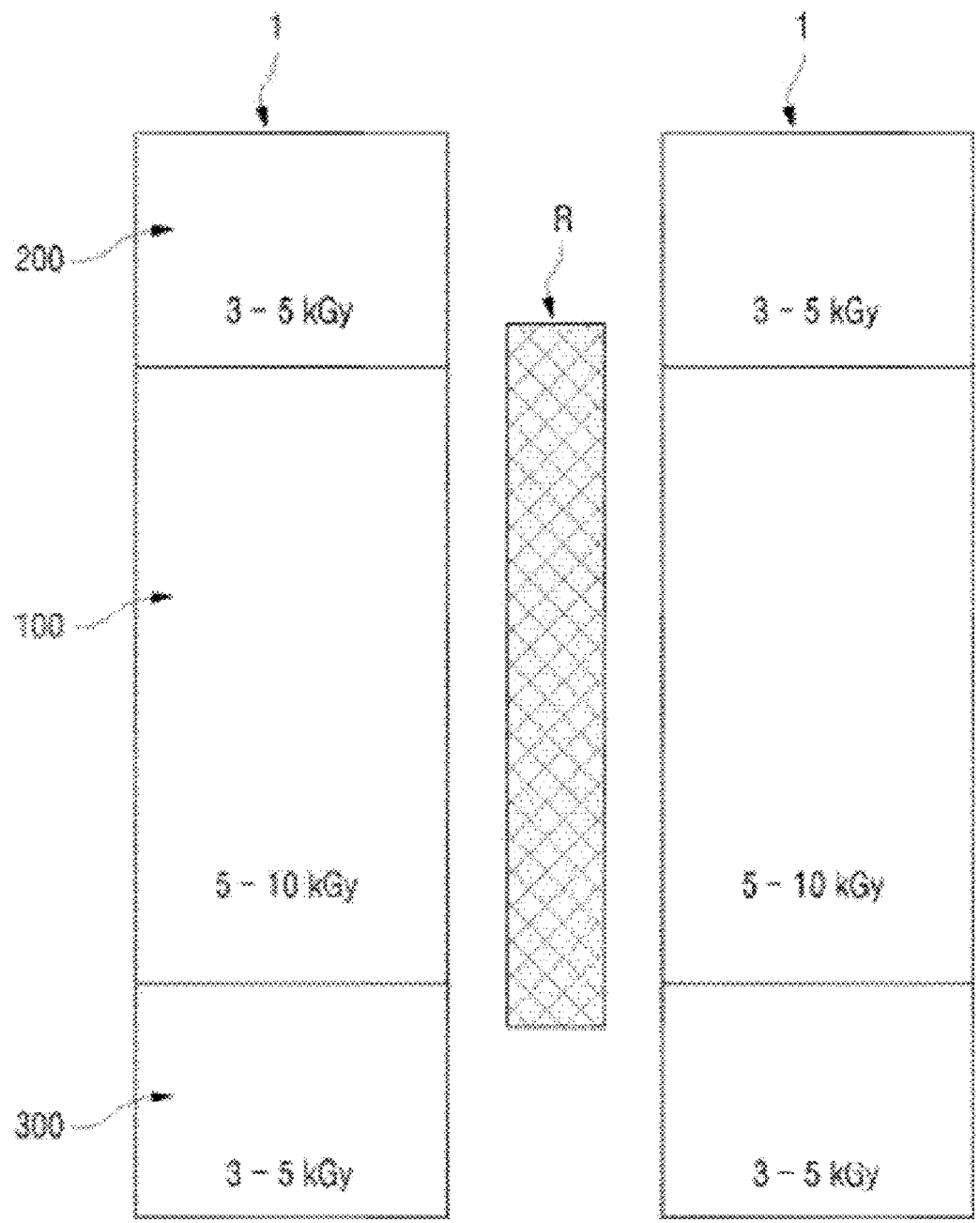

THREE-STAGE CARRIER FOR GAMMA IRRADIATION AND GAMMA IRRADIATION METHOD USING THREE-STAGE CARRIER

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/011938, filed Oct. 21, 2016, which claims priority to the benefit of Korean Patent Application No. 10-2015-0160349 filed in the Korean Intellectual Property Office on Nov. 16, 2015, the entire contents of which are incorporated herein by reference.

BACKGROUND

1. Technical Field

Example embodiments relate to a gamma irradiation technique.

2. Description of the Related Art

Generally, gamma ray (or, gamma radiation) is located near high energy portion in the electromagnetic radiation spectrum. The energy (or, intensity) of gamma ray is strong enough to destroy molecular bonds and to ionize atoms. However, the energy of the gamma ray is not strong to affect a structure of the nucleus. Therefore, the gamma ray changes chemical, physical or biological properties of a product being irradiated, but the product does not exhibit radioactivity.

Cobalt-60 and cesium-137 are the most suitable gamma ray sources (or gamma radiation sources) for radiation treatment because the cobalt-60 and the cesium-137 have high energy and a long half-life (e.g., 5.27 years for cobalt-60, 30.1 years for cesium-137). However, the cesium-137 is difficult to handle (or, to manage) because the cesium-137 has deliquescence at room temperature, which is exposed to air and absorbs moisture to dissolve. Therefore, the cesium-137 is not used for gamma irradiation on foods. Radiation treatment facilities in almost all industries use the cobalt-60 as the gamma ray.

Referring to FIG. 1, in a conventional gamma irradiation facility, a product to be irradiated is transferred and loaded on a carrier C by a forklift, and the carrier C is loaded on a conveyor 10 and sent to a irradiation room 20 (or a radiation room, radiation chamber).

A plurality of gamma ray sources of the cobalt-60 stored in a ray source rack R (or radiation source rack) are stored inside a storage room 30 (or, a shielded storage room) below the irradiation room 20. The storage room may be designed to be dry or wet. For example, because the gamma ray generated in the cobalt-60 is shielded at a depth of 4.5 m in water, the depth of a water tank is sufficient to be 6 to 7 m. The water in the water tank is circulated and purified by a water purification apparatus.

The irradiation room 20 is surrounded by a shielding wall 40 (or a radiation shield) of concrete having a thickness of about 2 m and is designed as a geometric maze so as to prevent radiation from leaking out to a outdoor place where a control console 50 is located.

The gamma ray sources shielded and stored in the storage room 30 is automatically raised from the water tank of the storage room 30 by a source hoist mechanism 60. The product loaded on the carrier C and moved to the inside of the irradiation room 20 through the conveyor 10 is continuously irradiated and sterilized and then is moved to the outside of the irradiation room 20 by the conveyor 10.

In addition, the gamma irradiation facility is designed as an interlock system so that an operator could not enter the irradiation room 20 during the irradiation process of the gamma ray sources. An automatic alarm system is activated when the radiation is leaked during the irradiation process.

Several types of gamma irradiation facilities have been developed considering a requirement to maximize energy utilization in the irradiation of the gamma ray sources, considering an importance of radiation source dose and absorption uniformity, and considering that different irradiation are required depending on the product.

For example, as illustrated in FIGS. 2 and 3, there are two types of a product overlay and a source overlay according to the ray source and the carrier.

Referring to FIG. 2, in the product overlay, carriers C form two layers and four rows on the conveyor 10 and move along periphery of the ray source rack R. The carriers C (or products loaded in the carriers C) can be moved between two layers by a lifting device (not shown). Here, height sum (or total height) of the carriers C in the two layers is greater than height of the ray source rack R. Therefore, in the product overlay, the absorption uniformity is maintained, the gamma ray energy irradiated from the source is not wasted, the products absorb energy as much as possible, and the energy utilization efficiency is high. However, in order for the products to exhibit a uniform dose distribution as a whole, the products stacked on upper side must be moved to lower side, and then the same irradiation process should be performed. This process is cumbersome and requires more than twice processing time.

Referring to FIG. 3, in the source overlay, the carriers C form one layer and a plurality of rows on the conveyor 10 and move along the periphery of the source rack R. The height of the carriers C is greater than the height of the carriers in the product overlay, but less than the height of the ray source rack R. Therefore, in the source overlay, strong gamma rays are emitted at the center of the ray source, and the irradiation is performed at a maximum dose, irradiation processing time of the product is shortened, and the absorption uniformity is similar to that of the product overlay. However, except for the gamma rays irradiated on the products, the remaining gamma rays are radiated to the air sot that the energy utilization efficiency is low.

However, conventional gamma ray irradiation facilities used commercially are designed and built in any one of product overlay type or source overlay type, and it is impossible to simultaneously use the product overlay and the source overlay during the gamma irradiation process in one facility.

SUMMARY

Some example embodiments provide a three-stage carrier for gamma irradiation and a gamma irradiation method using the three-stage carrier.

According to example embodiments, a three-stage carrier transported to an irradiation room by transporting means and irradiated with gamma ray sources installed on ray source rack such that a product loaded therein is treated. The three-stage carrier may include a central container in a center of the three-stage carrier; an upper container formed on the central container; and a lower container formed under the central container. Here, the central container, the upper container, and the lower container may be partitioned by septum, a height of the three-stage carrier may be greater than a height of the ray source lack, and the central container may have a height greater than a height of the upper container or a height of upper container.

In example embodiments, a drawer or a mesh pallet may be provided in each of the containers.

In example embodiments, the three-stage carrier may further include a double-sided opening-and-closing type door coupled to both front side of the three-stage carrier by hinges; and a bracket coupled to an upper end of the three-stage carrier. Here, a moving wheel is connected to the bracket such that the three-stage carrier is guided by a lower rail provided on a lower side of the three-stage carrier and movable along an upper rail provided on the upper side of the three-stage carrier.

According to example embodiments, a gamma irradiation method using a three-stage carrier which is transported to an irradiation room by transporting means and irradiated with gamma ray sources installed on ray source rack such that a product loaded therein is treated, the gamma irradiation method may include moving the three-stage carrier having a height greater than a height of ray source rack; and irradiating the product with a gamma ray. Here, a product loaded in the central container may have gamma ray irradiation effect of a source overlay, and a product loaded in the upper and lower containers may have gamma ray irradiation effect of a product overlay.

In example embodiments, a product requiring high dose irradiation may be loaded in the central container, and a product requiring maintenance of uniformity of sterilization effect may be loaded in the upper and lower containers. Here, the high dose irradiation may be performed to the central container and the low dose irradiation is performed to the upper and lower containers when the three-stage carrier is transported to the irradiation room and is irradiated with the gamma ray sources. Several types of products with different dose requirements may be simultaneously irradiated.

In example embodiments, a height of the product loaded in the upper container may be lowered to be irradiated with uniform dose.

Therefore, the three-stage carrier and the gamma ray irradiation method according to the present invention may simultaneously or selectively apply the source overlay and the product overlay.

In addition, the three-stage carrier and the gamma ray irradiation method may simultaneously process various kinds of products having different doses.

Furthermore, the three-stage carrier and the gamma ray irradiation method may ensure quality stability by uniform sterilization and may improve productivity in accordance with the simplification of the treatment process and the rapid treatment.

BRIEF DESCRIPTION OF THE DRAWINGS

Illustrative, non-limiting example embodiments will be more clearly understood from the following detailed description taken in conjunction with the accompanying drawings.

FIG. 11 is a diagram illustrating that a three-stage carrier is irradiated with different doses.

DETAILED DESCRIPTION

Hereinafter, the present inventive concept will be explained in detail with reference to the accompanying drawings.

cobalt-60, a radionuclide species, is used as the most common source of gamma rays in industrial and medical applications. The production of radioactive cobalt originates from natural cobalt metal, which is rich in stable isotope cobalt-59.

Figure 1:
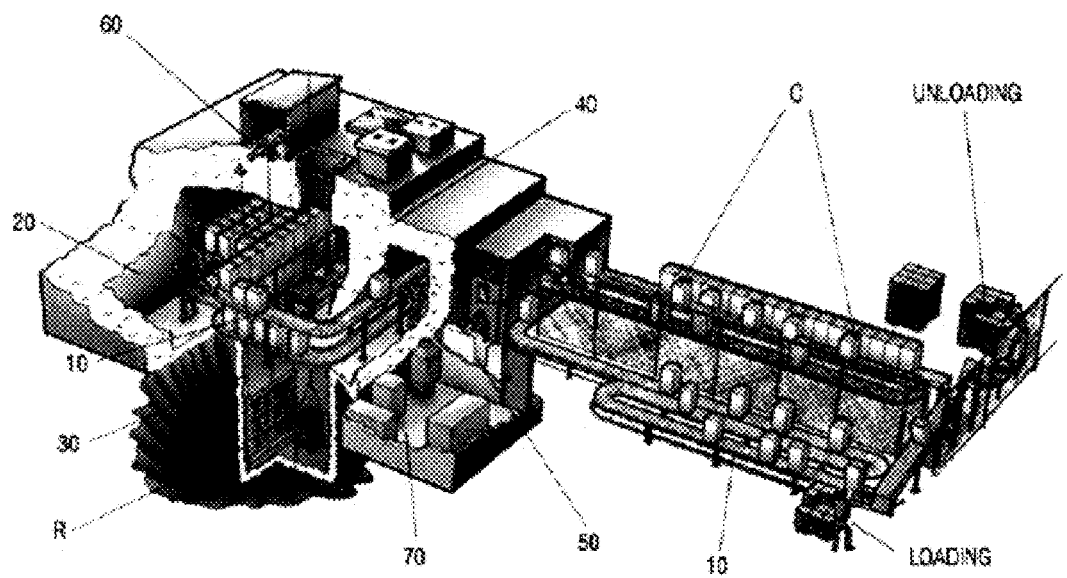
FIG. 1 is a diagram illustrating a gamma irradiation facility.
Figure 2:
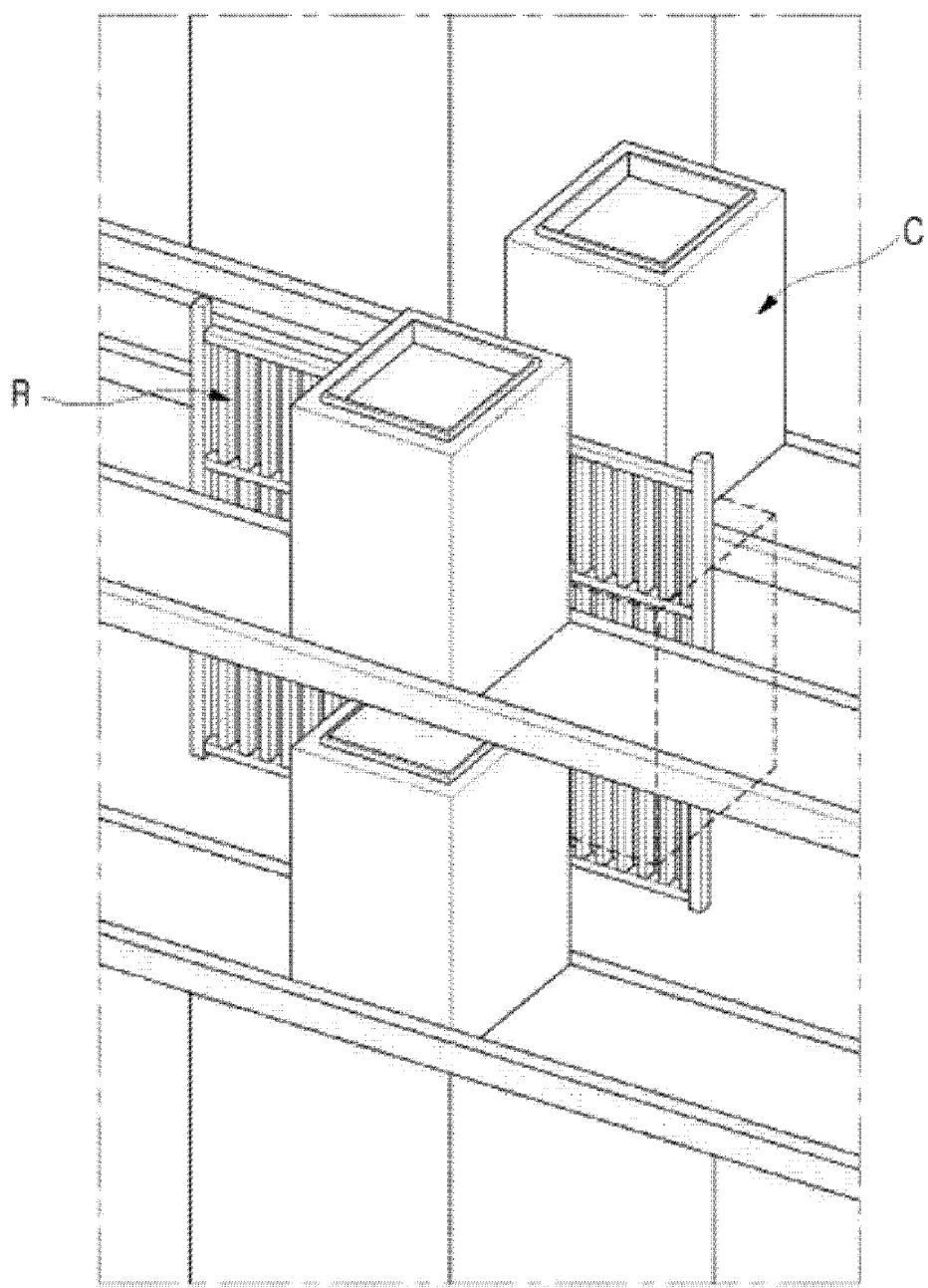
FIG. 2 is a diagram illustrating a irradiation type of a product overlay.
Figure 3:
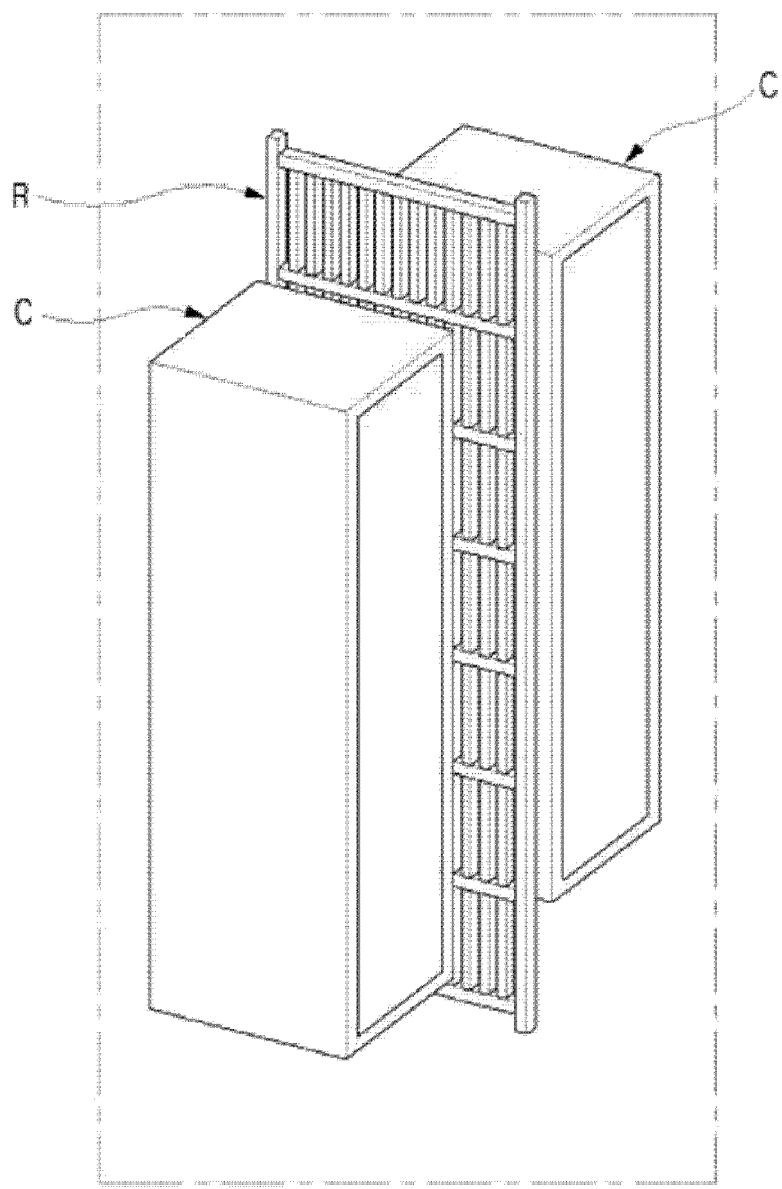
FIG. 3 is a diagram illustrating a irradiation type of a source overlay.
Figure 4:
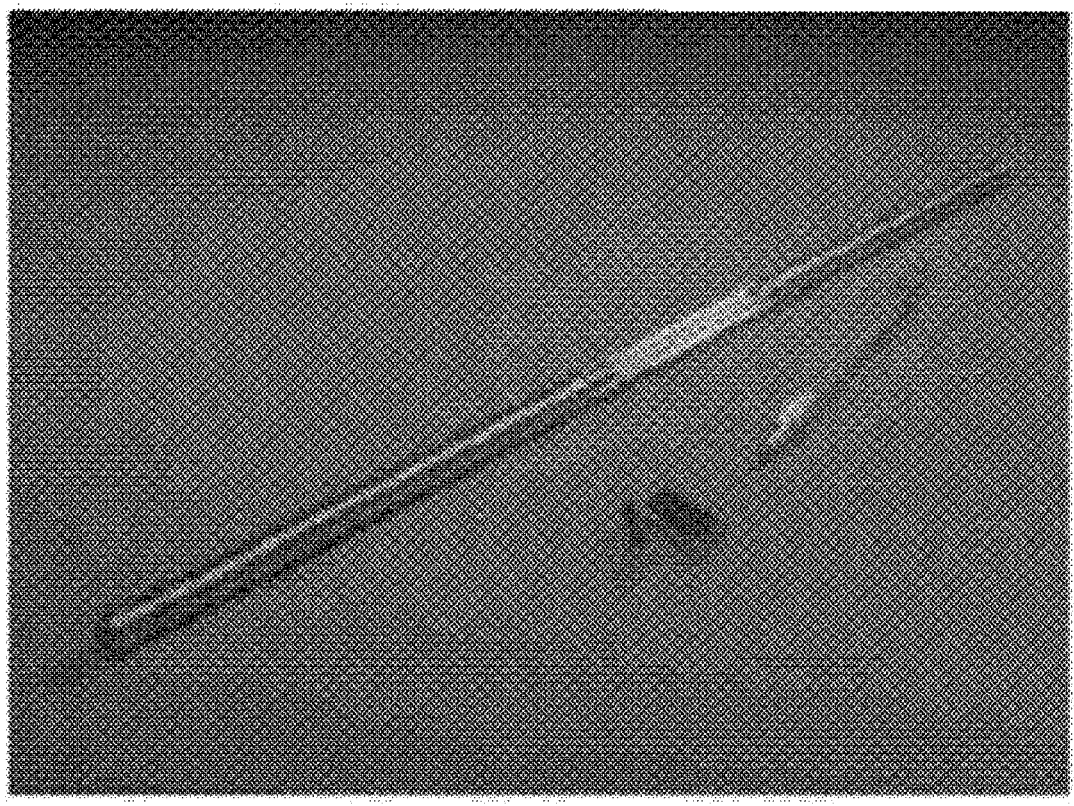
FIG. 4 is a diagram illustrating a slug and a pencil of cobalt-60.
Figure 5:
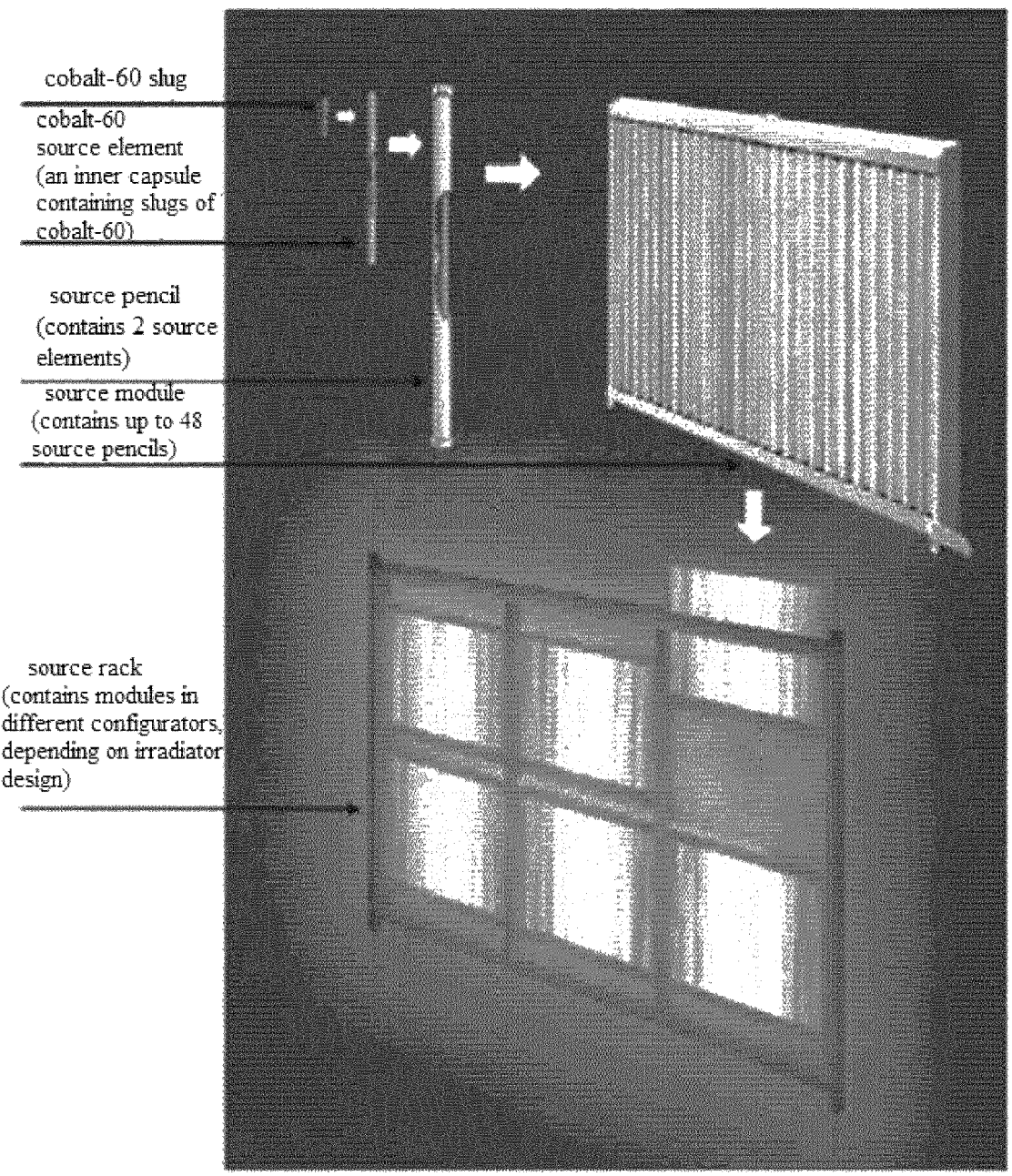
FIG. 5 is a diagram illustrating a build-up of cobalt-60 source rack.

99.9% pure cobalt sintered powder with a small cylinder shape is made, and a slug (or a cobalt slug) welded into a zirconium alloy capsule may remain in a reactor for about 18 to 24 months. During inside the reactor, a cobalt-59 atom absorbs neutrons and the cobalt-59 atom is converted to a cobalt-60 atom. In the cobalt slug, some of the atoms are converted to cobalt-60 atoms. Specific radioactivity (or, specific activity) is limited to approximately 120 Ci/g of the cobalt. As illustrated in FIG. 4, a capsule containing the cobalt slug is further encapsulated in stainless steel to be produced as a final source pencil in which gamma rays can be transmitted. Referring to FIG. 5, required gamma ray source is manufactured by loading such the source pencil into a predetermined position inside a source module. The source module is distributed over the ray source rack R of an industrial irradiation device (or irradiator).

Figure 6:
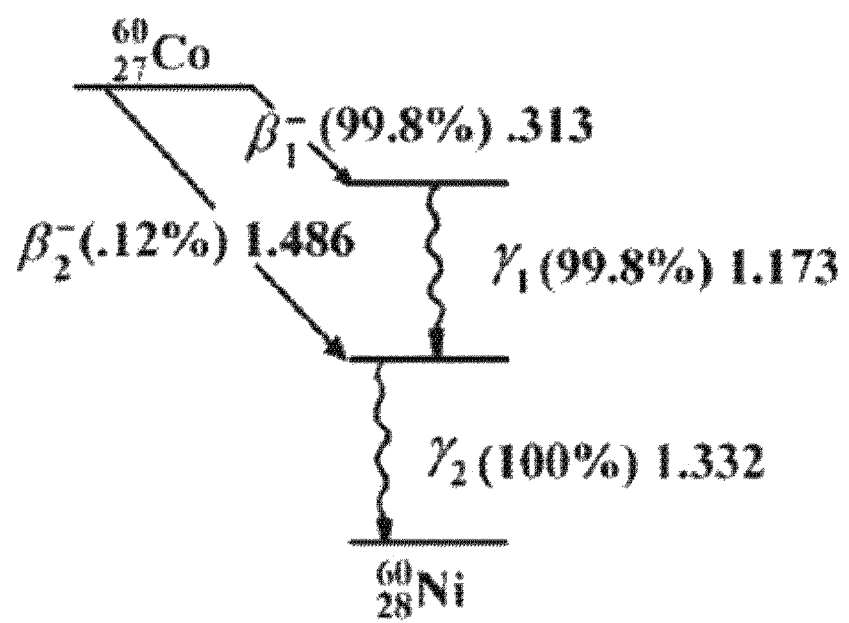
FIG. 6 is a diagram illustrating a decay process of cobalt-60 radionuclide.

Referring to FIG. 6, the cobalt-60 mainly emits one negative beta particle (e.g., with maximum energy of 0.313 MeV) and collapses into a stable nickel isotope having a half-life of 5.27 years. Then, the nickel (e.g., a nickel-60) is in an up-state and emits two photons of 1.17 to 1.33 MeV energy to reach a steady state immediately. Intensity or radioactivity level of the cobalt source is reduced to 50% in 5.27 at each cobalt-60 atomic collapse. The cobalt-60 source pencil is periodically added to the ray source rack to maintain a required capacity of the irradiation apparatus. The cobalt-60 source pencil is removed from the irradiation device when the cobalt-60 source pencil has reached its useful life of about 20 years.

A three-stage carrier 1 for gamma irradiation may loads with the product T, the three-stage carrier 1 may be transported to the irradiation room by transporting means, and the product T may be processed by the gamma ray irradiation with the above-mentioned gamma ray source. As a result, it is possible to simultaneously or selectively apply the source overlay and the product overlay, and uniform sterilization may be possible, and energy utilization efficiency and productivity due to rapid processing may be improved.

Figure 7:
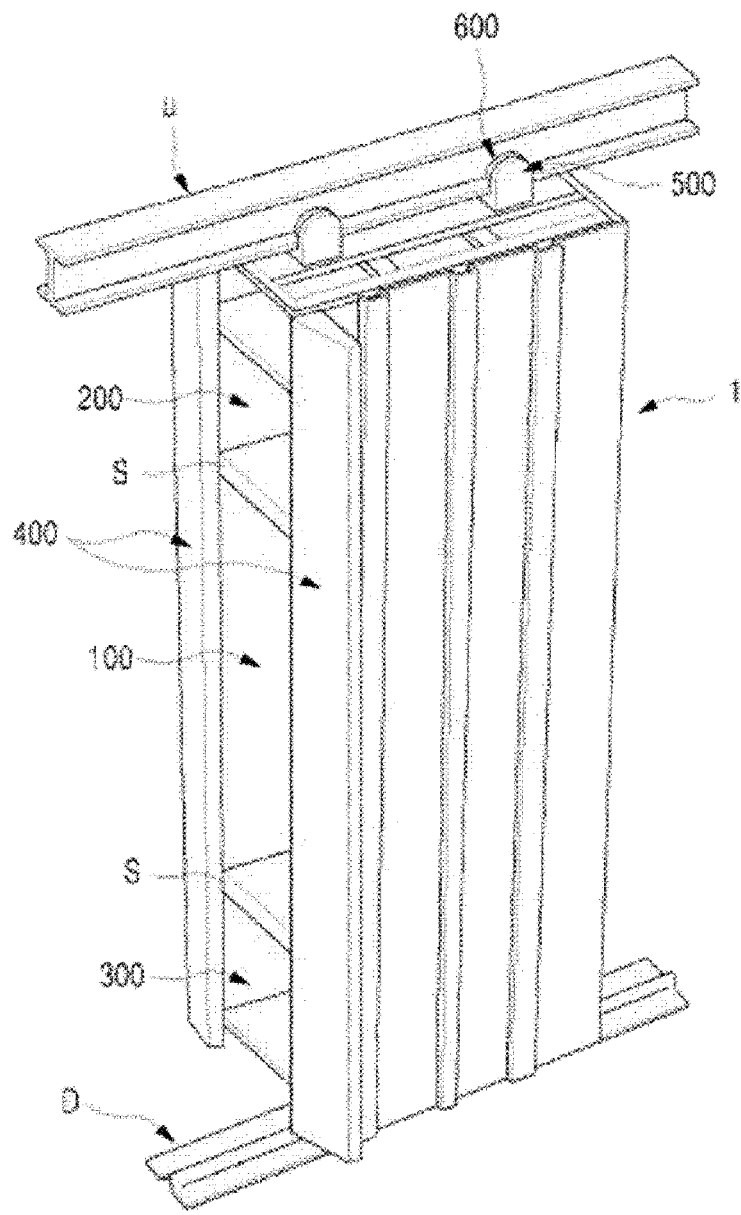
FIG. 7 is a perspective view illustrating a three-stage carrier according to example embodiment.
Figure 8:
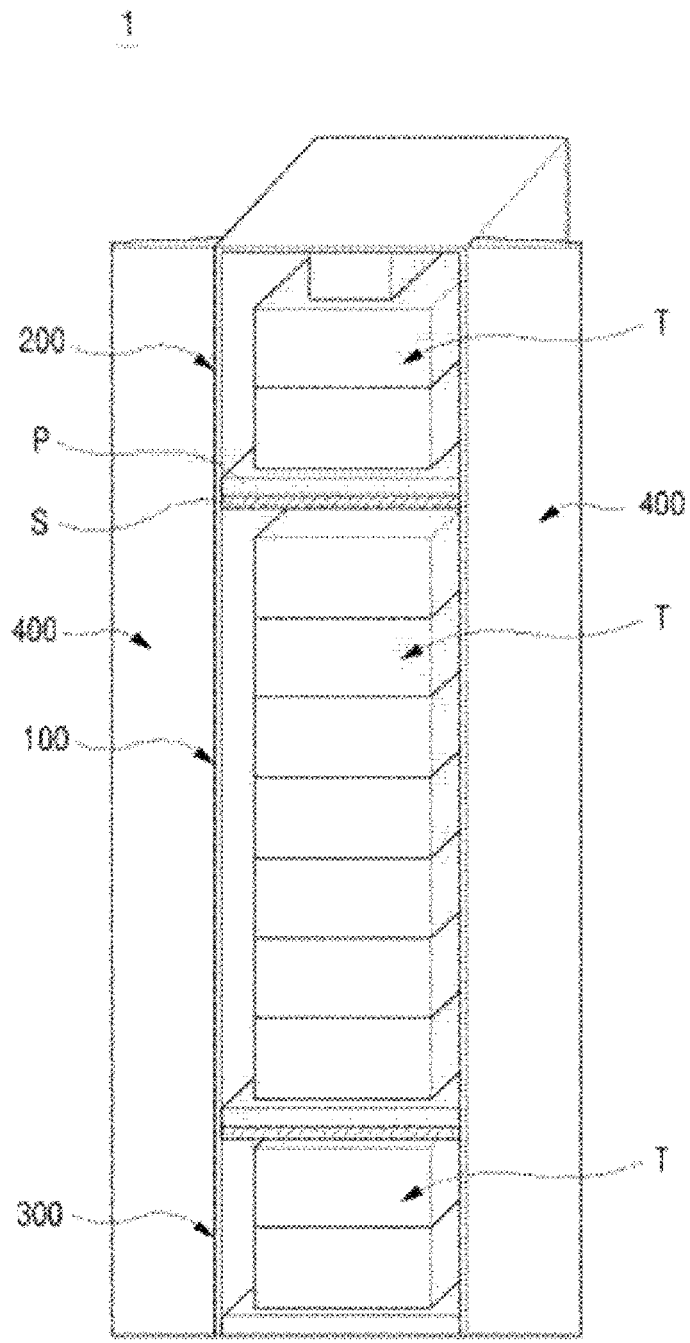
FIG. 8 is a diagram illustrating a three-stage carrier loading a product.

Referring to FIGS. 7 and 8, the three-stage carrier 1 may include a central container 100 at a central portion thereof, and an upper container 200 formed (or positioned) on an upper side of the central container 100 (or formed on or above the central container 100), and a lower container 300 formed on a lower side of the central container 100 (or formed under or below the central container 100). Here, the central container 100, the upper container 200, and the lower container 300 may be divided (or be portioned) by a septum S.

The three-stage carrier 1 may be formed to be higher (or larger, greater) than the ray source rack R. Therefore, when the three-stage carrier 1 having a height higher than that of the ray source rack R is transferred to the irradiation room along the conveying means while the product T is loaded therein, and when the three-stage carrier 1 moves around the ray source rack R, the product T may be irradiated with the source overlay and the product overlay at the same time.

The central container 100 may be formed to have a height greater than that of the upper container 200 or that of the lower container 300. Here, the product may be mass-processed, throughput per unit time may be greatly increased, and productivity may be improved.

Referring to FIG. 8, each of the containers 100, 200, and 300 of the three-stage carrier 1 may be provided with (or may include) a drawer or a pallet P on which a product is loaded so that the product T may be easily loaded. Preferably, the pallet may be a mesh pallet in a form of a mesh net so that gamma rays may be easily transmitted.

In an exemplary embodiment, a side door 400 may be hingably coupled (or connected) to both sides of a front side of the three-stage carrier 1, a plurality of brackets 500 may be coupled to an upper end of the three-stage carrier 1, and a moving wheel 600 may be connected to the brackets 500. The moving wheel 600 may be rotatably coupled to an upper rail U installed on a ceiling, and the three-stage carrier 1 may be movably installed along the upper rail U. In addition, a lower rail D may be provided below the three-stage carrier 1 to guide the movement of the three-stage carrier 1.

The present invention provides a gamma irradiation method using the three-stage carrier 1. As described above, the product T may be loaded into the central container 100, the upper container 200, and the lower container 300, the three-stage carrier may be transported to the irradiation room by the transporting means, and the product T may be processed by the gamma ray irradiation with the gamma ray source.

Figure 9:
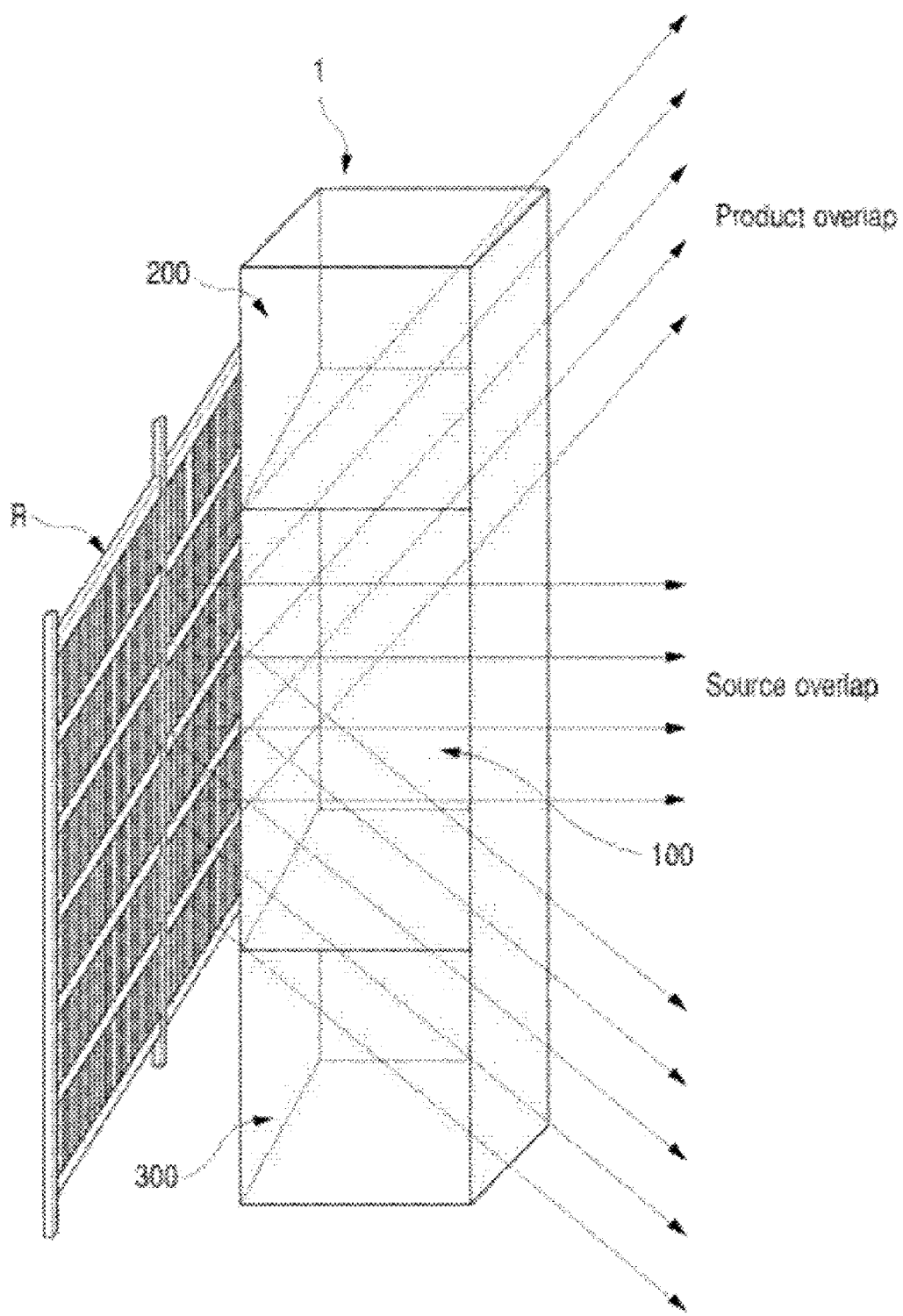
FIG. 9 is a diagram illustrating a source overlay and a product overlay to the three-stage carrier.

Referring to FIG. 9, the three-stage carrier 1 having a height greater than that of the source rack R may move around the ray source rack R, and the product T may be irradiated with gamma rays. Here, a gamma ray irradiation effect of the source overlay may appear on the product loaded on the central container 100 and irradiated, and a gamma ray irradiation effect of the product overlay may appear on the product loaded on the upper container 200 and on the lower container 300 and irradiated. That is, the method may have advantages of the source overlay and the product overlay at the same time, and the method may simultaneously or selectively apply (or use, perform) the source overlay and the product overlay. Therefore, a company requesting (or conducting) an irradiation of a product may have an option to select at least one of the product overlay and the source overlay. In addition, the company may increase economic benefits according to ensuring quality of the sterilized product and shortening delivery time.

Figure 10:
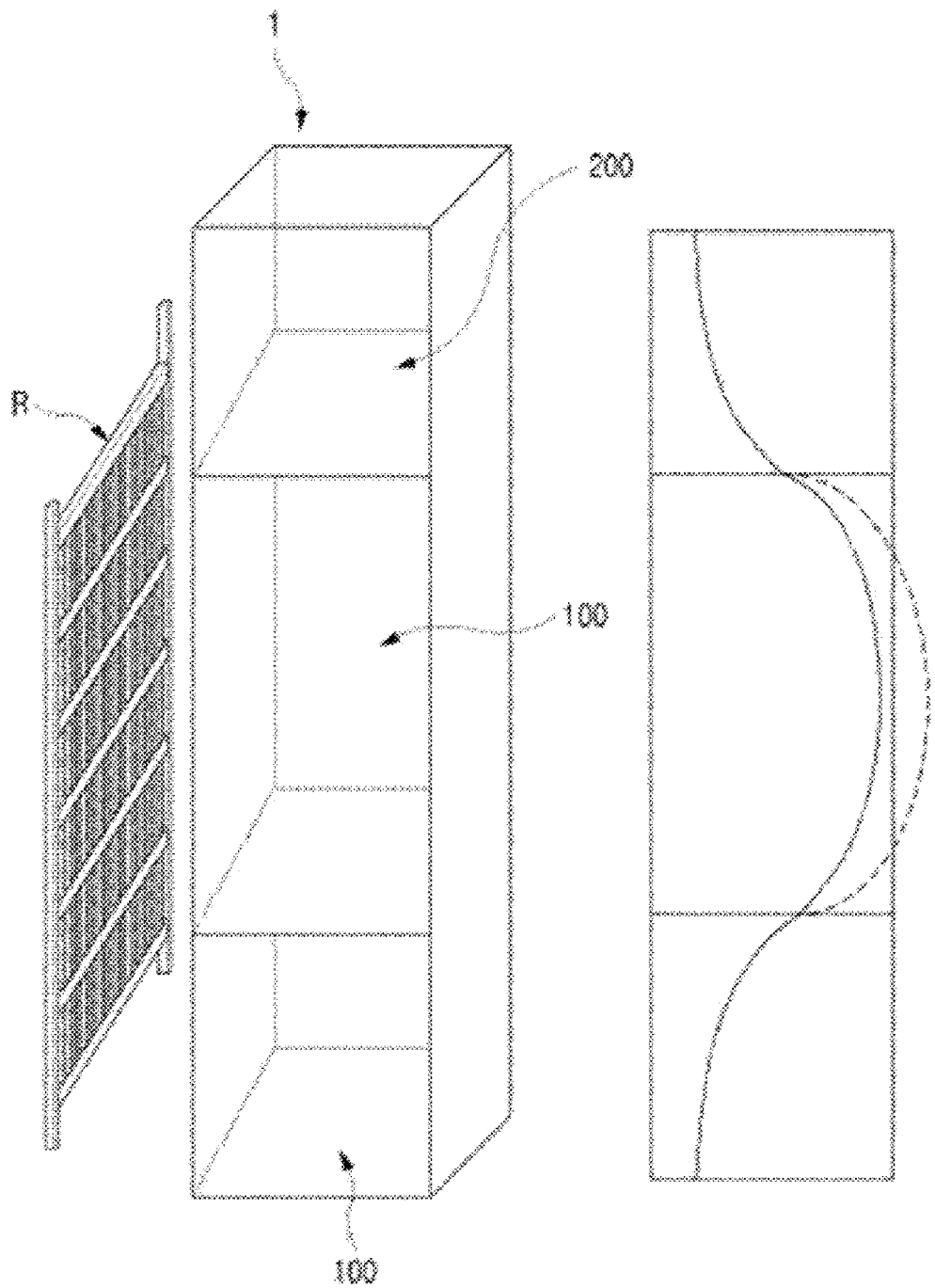
FIG. 10 is a diagram illustrating a dose distribution by position of a gamma ray source and the three-stage carrier.

Referring to FIG. 10, the gamma ray may show the highest dose at the center of the source due to the straightness of rays. In dose distribution, the central container 100 may exhibit a relatively uniform dose distribution with a high dose, and the upper container 200 and the lower container 300 may exhibit a relatively uniform dose distribution with a relatively low dose.

In addition, amount of irradiation in the central container 100 may be 50% higher than that in the conventional irradiation because the central container 100 is formed larger than other containers (i.e., the upper and lower containers 200 and 300) and the gamma rays are straight.

Products loaded in upper portion or in lower portion of conventional carrier are vertically exchanged through the lifting device to perform uniform irradiation. However, there is no need to perform the above-mentioned product replacement operation at the upper and lower portions in the present invention. Because the lifting device is not used during irradiation process, it is possible to prevent breakage and malfunction of the product during the process. In addition, the sterilization irradiation on the product may be performed rapidly in a short time with high and uniform dose in the central container 100.

In an exemplary embodiment, a product requiring high-dose irradiation may be loaded in the central container 100, and a product requiring low dose irradiation and maintaining uniformity of the sterilization effect may be loaded in the upper container 200 and/or the lower container 300. Thereafter, the three-stage carrier 1 may be transferred to the irradiation room, and the products may be treated by irradiation with gamma rays by the gamma ray source. Here, the central container 100 may be irradiated with a high dose, and the upper container 200 and the lower container 300 may be irradiated uniformly with a low dose. That is, it is possible to simultaneously process various types of products having different doses.

When a height of the product to be loaded in the upper container 200 is lowered, a uniform dose may be irradiated. That is, in the irradiation type of the product overlay, loaded amount (or stacking amount) of the product is smaller, effect of permeation of the gamma ray may be larger. Thus, the dose uniformity both inside and outside may be improved (or increased). The dose uniformity more be processed (or adjusted) to a desired specification.

Table 1 shows a processing time and a daily production amount of the gamma irradiation method according to the present invention compared with those of conventional method of the product overlay and the source overlay.

TABLE 1

| | Irradiation type | Density | Dose range | Up/down rotation (rotation number) | Processing time | Daily production | Total daily production |
|---|---|---|---|---|---|---|---|
| Present invention (three-stage carrier) | Upper/lower container | 0.15 | 3-5 | | 3:35 | 227 | 681 |
| | Central container | 0.15 | 6-10 | | 3:35 | 454 | |

TABLE 1-continued

| Irradiation type | | Density | Dose range | Up/down rotation (rotation number) | Processing time | Daily production | Total daily production |
|---|---|---|---|---|---|---|---|
| Conventional | Product | 0.15 | 3-5 | 1 | 3:35 | 227 | 340.5 |
| invention | overlay | 0.15 | 6-10 | 2 | 7:10 | 113.5 | |
| | Source | 0.15 | 3-5 | | 1:57.5 | 454 | 567.5 |
| | overlay | 0.15 | 6-10 | | 7:10 | 113.5 | |

* Set time is 3 m 10 s, and doses of target products are 5 kGy and 10 kGy (where, except for an initial rotation time)

As can be seen in Table 1, the gamma ray irradiation method according to the present invention may simultaneously or selectively apply the source overlay and the product overlay using the three-stage carrier 1. In addition, the gamma ray irradiation method according to the present invention may simultaneously process various kinds of products having different doses. Furthermore, the gamma ray irradiation method according to the present invention may ensure quality stability by uniform sterilization and may improve productivity in accordance with the simplification of the treatment process and the rapid treatment.

The foregoing is illustrative of example embodiments, and is not to be construed as limiting thereof. Although a few example embodiments have been described, those skilled in the art will readily appreciate that many modifications are possible in the example embodiments without materially departing from the novel teachings and advantages of example embodiments. Accordingly, all such modifications are intended to be included within the scope of example embodiments as defined in the claims. In the claims, means-plus-function clauses are intended to cover the structures described herein as performing the recited function and not only structural equivalents but also equivalent structures. Therefore, it is to be understood that the foregoing is illustrative of example embodiments and is not to be construed as limited to the specific embodiments disclosed, and that modifications to the disclosed example embodiments, as well as other example embodiments, are intended to be included within the scope of the appended claims. The inventive concept is defined by the following claims, with equivalents of the claims to be included therein.

What is claimed is:

1. A three-stage carrier transported to an irradiation room by transporting means and irradiated with gamma ray sources installed on a ray source rack such that a product loaded therein is treated, the three-stage carrier comprising:
 a central container in a center of the three-stage carrier; an upper container formed on the central container; and a lower container formed under the central container,
 wherein the central container, the upper container, and the lower container are partitioned by septums;
 a height of the three-stage carrier is greater than a height of the ray source rack; and
 the central container has a height greater than a height of the upper container or a height of the lower container.

2. The three-stage carrier of claim 1, wherein a drawer or a mesh pallet is housed in each of the containers.

3. The three-stage carrier of claim 1 further comprising:
 a double-sided opening-and-closing type door coupled to both front side of the three-stage carrier by hinges; and
 a bracket coupled to an upper end of the three-stage carrier,
 wherein a moving wheel is connected to the bracket such that the three-stage carrier is guided by a lower rail provided on a lower side of the three-stage carrier and movable along an upper rail provided on the upper side of the three-stage carrier.

4. A gamma irradiation method using the three-stage carrier of claim 1, the gamma irradiation method comprising:
 moving the three-stage carrier having a height greater than a height of a ray source rack; and
 irradiating the product with a gamma ray,
 wherein a product loaded in the central container has a gamma ray irradiation effect of a source overlay; and
 a product loaded in the upper and lower containers has a gamma ray irradiation effect of a product overlay.

5. The gamma irradiation method of claim 4, wherein a product requiring high dose irradiation is loaded in the central container,
 wherein a product requiring maintenance of uniformity of sterilization effect is loaded in the upper and lower containers;
 the high dose irradiation is performed to the central container and the low dose irradiation is performed to the upper and lower containers when the three-stage carrier is transported to the irradiation room and is irradiated with the gamma ray sources; and
 several types of products with different dose requirements are simultaneously irradiated.

6. The gamma irradiation method of claim 4, wherein a height of the product loaded in the upper container is lowered to be irradiated with uniform dose.

* * * * *